United States Patent [19]

Jaehne et al.

[11] Patent Number: 5,457,091
[45] Date of Patent: Oct. 10, 1995

[54] N1-SUBSTITUTED 1H-1,2,3-TRIAZOLO[4,5,-D]PYRIMIDINES, A PROCESS FOR THEIR PREPARATION AND THEIR USE AS ANTIVIRAL AGENTS

[75] Inventors: Gerhard Jaehne, Frankfurt; Matthias Helsberg, Kelkheim/Ts.; Irvin Winkler, Liederbach; Gerhard Gross, Floersheim/M.; Thomas Scholl, Frankfurt, all of Germany

[73] Assignee: Hoechst Aktiengesellschaft, Frankfurt am Main, Germany

[21] Appl. No.: 125,195

[22] Filed: Sep. 23, 1993

[30] Foreign Application Priority Data

Sep. 24, 1992 [DE] Germany .............. 42 31 944.7

[51] Int. Cl.⁶ .............. A61K 31/505; C07D 239/00
[52] U.S. Cl. .............. 514/81; 514/258; 544/224; 544/254
[58] Field of Search .............. 544/254, 224; 514/258, 81

[56] References Cited

U.S. PATENT DOCUMENTS

| | | | |
|---|---|---|---|
| 4,027,025 | 5/1977 | Schaeffer | 514/258 |
| 4,199,574 | 4/1980 | Schaeffer | 424/200 |
| 4,268,672 | 5/1981 | Vince | 544/265 |
| 4,294,831 | 10/1981 | Schaeffer | 424/253 |
| 4,323,573 | 4/1982 | Schaeffer | 424/253 |
| 4,360,422 | 11/1982 | Oka et al. | 209/5 |
| 4,543,255 | 9/1985 | Shealy et al. | 514/258 |
| 4,714,701 | 12/1987 | Beauchamp | 514/258 |
| 4,728,736 | 3/1988 | Shealy et al. | 514/258 |
| 4,742,064 | 5/1988 | Vince | 514/258 |
| 5,225,550 | 7/1993 | Jahne | 544/277 |

FOREIGN PATENT DOCUMENTS

| | | |
|---|---|---|
| 0201289A3 | 11/1986 | European Pat. Off. . |
| 0452680A1 | 10/1991 | European Pat. Off. . |
| 0464511A2 | 1/1992 | European Pat. Off. . |
| 2539963C2 | 3/1976 | Germany . |
| 4020481A1 | 1/1992 | Germany . |
| 59-080685 | 8/1984 | Japan . |
| WO90/06312 | 6/1990 | WIPO . |

OTHER PUBLICATIONS

Beauchamp et al., Journal of Medicinal Chemistry, 1985, 28(8): 982–987.

K. Ogilvie et al., "Synthesis of a Purine Acyclonucleoside Series Having Pronounced Antiviral Activity. The Glyceropurines," Can. J. Chem. 62, pp. 241–252 (1984).

C. Chu et al., "Chemistry and Antiviral Activities of Acyclonucleosides," J. Heterocyclic Chem. 23, pp. 289–319 (1986).

J. Stein et al., "Inhibition of Human Purine Nucleoside Phosphorylase By Acyclic Nucleosides and Nucleotides," Biochem. Pharmacol. 36, pp. 1237–1244 (1987).

CA 53, 1389g (1959).

L. Beauchamp et al., "Modifications on the Heterocyclic Base of Acyclovir: Synthesis and Antiviral Properties," J. Med. Chem. 28, pp. 982–987 (1985).

A. Colautti et al., "Zusammenfassung," Chemical Abstracts, vol. 75, No. 13, abstract No. 88567x, cite 710–717 (1971).

F. Seela et al., "Zusammenfassung," Chemical Abstracts, vol. 118, No. 7, abstract No. 60018b, cite 1885–1896 (1993).

Primary Examiner—Mukund J. Shah
Assistant Examiner—Matthew V. Grumbling
Attorney, Agent, or Firm—Finnegan, Henderson, Farabow, Garrett & Dunner

[57] ABSTRACT

N1-Substituted 1H-1,2,3-triazolo[4,5-d]pyrimidine compounds of the formula I

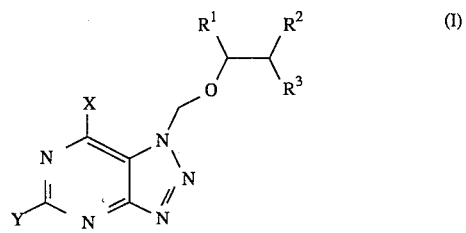

in which the substituents X, Y, $R^1$, $R^2$ and $R^3$ have the meanings recited in the specification, are described as pharmaceutical compositions containing them and processes for their preparation. The compounds are effective antiviral agents.

8 Claims, No Drawings

N1-SUBSTITUTED 1H-1,2,3-TRIAZOLO[4,5,-D]PYRIMIDINES, A PROCESS FOR THEIR PREPARATION AND THEIR USE AS ANTIVIRAL AGENTS

DESCRIPTION

N1-Substituted 1H-1,2,3-triazolo[4,5-d]pyrimidines, a process for their preparation and their use as antiviral agents.

The present invention relates to derivatives of 1H-1,2,3-triazolo[4,5-d]pyrimidine which have an alkoxymethyl radical in position 1, to processes for preparing these compounds, and to their use as antiviral agents. In particular, the invention relates to those 1H-1,2,3triazolo[ 4,5-d]pyrimidines which are substituted by an alkoxymethyl radical in position 1 and have an amino group in position 5 and are substituted by hydrogen, halogen, hydroxyl, alkoxy, amino, mercapto or alkylthio in position 7. Furthermore, the invention relates to the physiologically tolerated salts of the said compounds.

Whereas the antiviral activity and the preparation of purine nucleoside analogs which have an acyclic radical in position 9 have been known for a long time (see, for example, DE-A 2539963 or K. K. Ogilvie et al., Can. J. Chem. 62, 241 (1984) or C. K. Chu and S. J. Cutler, J. Heterocyclic Chem. 23,289 (1986)) and the preparation of individual compounds with an acyclic radical in position 3 of 5-amino-7-hydroxy-3H-1,2,3-triazolo[4,5-d]pyrimidine is also described (see L. M. Beauchamp et al., J. Med. Chem. 28, 982 (1985) or J. M. Stein et al., Biochem. Pharmacol. 36, 1237 (1987)), only little is known about the synthesis of 1H-1,2,3-triazolo[4,5-d]pyrimidines which have an acyclic radical in position I (see Chemical Abstracts 53, 1389g (1959) and L. M. Beauchamp et al., J. Med. Chem. 28, 982 (1985)) and there has been no report to date of an antiviral action of those compounds in which the acyclic radical is a possibly substituted 2-hydroxyethoxymethyl or 1,3-dihydroxy-2-propoxymethyl or 2,3-dihydroxy-1-propoxymethyl radical.

It has now been found, surprisingly, that certain 1-substituted 1H-1,2,3-triazolo[4,5-d]pyrimidines and their physiologically tolerated salts have antiviral properties, especially against various DNA viruses, RNA viruses and retroviruses.

The invention accordingly relates to compounds of the formula I

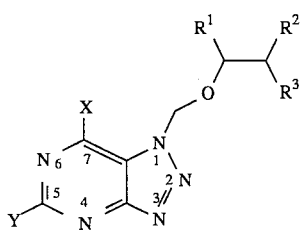

and their tautomeric forms, in which

X is hydrogen, halogen, hydroxyl, $C_1$-$C_6$-alkoxy, benzyloxy, phenoxy, mercapto, $C_1$-$C_6$-alkylthio, benzylthio, phenylthio or amino, Y is amino, $C_1$-$C_8$-acylamino, $C_1$-$C_8$-thioacylamino, $C_2$-$C_{16}$-diacylamino, $C_2$-$C_{16}$-di(thioacyl) amino, $(C_1$-$C_4$-alkyl)$_2$-N-CH=N- or N-$(C_1$-$C_4$-alkyl) pyrrolidinylidene-N-, $R^1$ is hydrogen, $C_1$-$C_6$-alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P(O) (OR$^5$) (OR$^6$) or -O-CH$_2$-P (O) (OR$^5$) (OR$^6$) in which $R^5$ and $R^6$ are, independently of one another, hydrogen or a $C_1$-$C_6$-alkyl radical or ammonium or triethylammonium or an alkali metal ion, $R^2$ is hydrogen, $C_1$-$C_6$-alkyl, hydroxyl, amino, mercapto, halogen, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy; $C_1$-$C_8$-acylamino, $C_1$-$C_8$-acylthio or -O-CH$_2$-P (O) (OR$^5$) (OR$^6$) where the radicals $R^5$ and $R^6$ are as defined above, and $R^3$ is hydrogen, $C_1$-$C_6$-alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzyl amino, phenoxy, phenylthio, $C_1$-$C_8$-acyloxy, $C_1$-$C_8$-acylamino or $C_1$-$C_8$-acylthio group or by a radical $R^4$ where $R^4$ is -P (O) (OR$^5$) (OR$^6$) or -O-CH$_2$-P (O) (OR$^5$) (OR$^6$) in which $R^5$ and $R^6$ are, independently of one another, hydrogen or a $C_1$-$C_6$-alkyl radical or ammonium, triethylammonium or an alkali metal ion, and their physiologically tolerated salts and evident chemical equivalents with the proviso that X is not hydroxyl when $R^1$ and $R^3$ are hydrogen and $R^2$ is benzoyloxy.

Preferred compounds of the formula I are those in which

X is hydrogen, hydroxyl, $C_1$-$C_6$-alkoxy, benzyloxy, mercapto or amino,

Y is amino, $C_1$-$C_3$-acylamino, $C_1$-$C_3$-thioacylamino, $C_2$-$C_6$-diacylamino, $C_2$-$C_6$-di(thioacyl) amino, $(CH_3)_2$-N-CH=N- or N- $(CH_3)$ -pyrrolidinylidene-N-, $R^1$ is hydrogen, $C_1$-$C_3$-alkyl optionally substituted by a hydroxyl, $C_1$-$C_6$-alkoxy or $C_1$-$C_6$-acyloxy group or by a radical $R^4$ where $R^4$ is -P (O) (OR$^5$) (OR$^6$) or -O-CH$_2$-P (O) (OR$^5$) (OR$^6$) in which $R^5$ and $R^6$ are, independently of one another, hydrogen or a $C_1$- $C_6$ - alkyl radical or ammonium or triethylammonium or an alkali metal ion, $R^2$ is hydrogen, hydroxyl, $C_1$-$C_6$-alkoxy or $C_1$-$C_8$-acyloxy or -O-CH$_2$-P (O) (OR$^5$) (OR$^6$) where the radicals $R^5$ and $R^6$ are as defined above, and $R^3$ is hydrogen or $C_1$-$C_4$-alkyl optionally substituted by a hydroxyl, $C_1$-$C_6$-alkoxy or $C_1$-$C_8$-acyloxy group or by a radical $R^4$ where $R^4$ is -P (O) (OR$^5$) (OR$^6$) or -O-CH$_2$-P (O) (OR$^5$) (OR$^6$) in which $R^5$ and $R^6$ are, independently of one another, hydrogen or a $C_1$-$C_6$-alkyl radical or ammonium, triethylammonium or an alkali metal ion.

Particularly preferred compounds of the formula I are those in which

X is hydrogen, hydroxyl, SH or amino,

Y is amino or $C_1$-$C_3$-acylamino, $R^1$ is $C_1$-$C_3$-alkyl optionally substituted by a hydroxyl, $C_1$-$C_3$-alkoxy or $C_1$-$C_8$-acyloxy group, $R^2$ is hydroxyl, $C_1$-$C_3$-alkoxy or $C_1$-$C_3$-acyloxy, and $R^3$ is hydrogen.

Further particularly important compounds of the formula I are those in which

X is hydrogen,

Y is amino, $R^1$ is $C_1$-$C_3$-alkyl optionally substituted by a hydroxyl, $C_1$-$C_3$-alkoxy or $C_1$-$C_8$-acyloxy group or by a radical $R^4$ where $R^4$ is -P(O)(ORs)(OR$^6$) or -O-CH$_2$-P(O)(OR$^5$)(OR$^6$) in which $R^5$ and $R^6$ are, independently of one another, hydrogen or a $C_1$-$C_6$-alkyl radical or ammonium or triethylammonium or an alkali metal ion, $R^2$ is hydroxyl, $C_1$-$C_3$-alkoxy or $C_1$-$C_3$-acyloxy, and $R^3$ is hydrogen.

Further very particularly important compounds of the formula I are those in which X is hydrogen,
Y is amino,
$R^1$ is hydroxymethyl, $C_1$-$C_5$-acyloxymethyl or $C_1$-$C_3$-alkoxymethyl,
$R^2$ is hydroxyl, $C_1$-$C_3$-alkoxy or $C_1$-$C_3$-acyloxy, and
$R^3$ is hydrogen.

The alkyl groups or functionalized alkyl group such as, for example, acyl, alkoxy, alkylthio etc. mentioned as substituents of the above formula I can be branched or unbranched or cyclic. Examples of alkyl groups are the methyl, ethyl, propyl, isopropyl, butyl or isobutyl group. Examples of alkoxy groups are the methoxy, ethoxy, propoxy, isopropoxy, butoxy or cyclopentyloxy group.

Preferred acyl groups are the acetyl, propionyl, butyryl, isobutyryl, valeroyl and benzoyl group, as well as the methoxycarbonyl, ethoxycarbonyl or the isopropoxycarbonyl group, as well as, furthermore, the cyclic carbonate when 1,3-diol structures are present such as, for example, when $R^1$ is hydroxymethyl and $R^2$ is hydroxyl.

The preferred halogen substituent is chlorine. A particularly suitable alkali metal substituent is sodium.

The compounds of this invention are in their entirety substituted acyclic 1H-1,2,3-triazolo[4,5-d]pyrimidines which have the acyclic substituent in position 1 of the 1H-1,2,3-triazolo[4,5-d]pyrimidine ring system.

Salts of the compounds according to the invention which are particularly suitable for therapeutic purposes are salts of physiologically tolerated organic and inorganic acids such as acetic acid, lactic acid, malic acid, p-toluenesulfonic acid, methanesulfonic acid, isethionic acid, hydrochloric acid or sulfuric acid.

Evident chemical equivalents of the compounds according to the invention are, in particular, derivatives thereof which can be converted without difficulty, for example under physiological conditions, into the compounds according to the invention. Particularly preferred compounds of the formula I according to the invention are 5-amino-1H-1-[(1,3-bisisopropoxy-2-propoxy)methyl] 1,2,3-triazolo[4,5-d]pyrimidine (Example 7; compound of the formula I in which X is hydrogen, Y is amino, $R^1$ is isopropoxymethyl, $R^2$ is isopropoxy and $R^3$ is hydrogen), 5-amino-1H-1-[(1,3 -diacetoxy-2 -propoxy)methyl]-1,2,3-triazolo [4,5 -d] pyrimidine (Example 10; compound of the formula I in which X is hydrogen, Y is amino, $R^1$ is acetoxymethyl, $R^2$ is acetoxy and $R^3$ is hydrogen) and 5-amino-1H-1-[(1,3-dihydroxy-2-propoxy)methyl]-1,2,3-triazolo[ 4,5-d]pyrimidine (Example 9; compound of the formula I in which X is hydrogen, Y is amino, $R^1$ is hydroxymethyl, $R^2$ is hydroxyl and $R^3$ is hydrogen), especially because of their particularly high activity against herpesviruses.

Furthermore, other compounds of the formula I with X=hydrogen and an acyclic side-chain whose hydroxyl group or hydroxyl groups are etherified with $C_1$-$C_6$-alkyl radicals or esterified with $C_1$-$C_6$-acyl radicals display particularly high antiviral activity.

The invention furthermore relates to the use of the said compounds as pharmaceuticals. The compounds according to the invention are particularly effective against type 1 and type 2 herpes simplex viruses, cytomegaloviruses, varicella zoster viruses, Epstein-Barr viruses and type 6 human herpes virus (HHV 6).

The present invention furthermore relates to the use of the abovementioned compounds of the formula I—where X can also be hydroxyl when $R^1$ and $R^3$ are hydrogen and $R^2$ is benzoyloxy—for the production of pharmaceuticals for the prophylaxis or for the treatment of vital diseases.

The present invention furthermore relates to a process for the regioselective preparation of 1H-1,2,3-triazolo[ 4,5-d] pyrimidines of the formula I which are substituted in position 1 or of a physiologically tolerated salt thereof, which comprises reacting a compound of the formula II

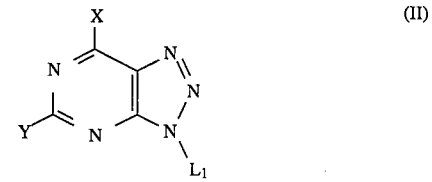

in which
X is hydrogen, $C_1$-$C_6$-alkoxy, benzyloxy, trialkylsilyloxy, trialkylsilylthio, $C_1$-$C_6$-acyl(trialkylsilyl)-amino, trialkylsilylamino, $C_1$-$C_3$-alkylthio or halogen, preferably trimethylsilyloxy,
Y is trialkylsilylmmino, $C_1$-$C_6$-acylamino, $C_2$-$C_{12}$-diacylamino or $C_1$-$C_6$-acyl(trialkylsilyl)amino, preferably trimethylsilylacetamido,
and the leaving group $L_1$ is acyloxy or trialkylsilyl, preferably trimethylsilyl,
with a compound of the formula III

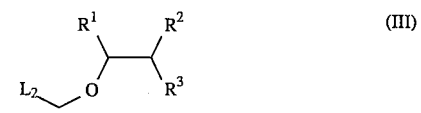

in which
$R^1$ is hydrogen, $C_1$-$C_6$-alkyl optionally substituted by halogen or by a $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P(O) $(OR^5)$ $(OR^6)$ or -O-$CH_2$-P (O) $(OR^5)$ $(OR^6)$ in which $R^5$ and $R^6$ are, independently of one another, a $C_1$-$C_6$-alkyl radical,
$R^2$ is hydrogen, $C_1$-$C_6$-alkyl, halogen, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino, $C_1$-$C_8$-acylthio or -O-$CH_2$-P(O) $(OR^5)$ $(OR^6)$ where the radicals $R^5$ and $R^6$ are as defined above, and
$R^3$ is hydrogen, $C_1$-$C_6$-alkyl optionally substituted by halogen or by a $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P (O) $(OR^5)$ $(OR^6)$ or -O-$CH_2$-P (O) $(OR^5)$ $(OR^6)$ in which $R^5$ and $R^6$ are, independently of one another, a $C_1$-$C_6$-alkyl radical, and the leaving group $L_2$ is halogen, preferably chlorine, or the $C_1$-$C_6$-alkylthio or $C_1$-$C_6$-alkylsulfinyl or $C_1$-$C_6$-alkylsulfonyl group, preferably the methylthio or the methylsulfinyl or the methylsulfonyl group, or $C_1$-$C_8$-acyloxy or benzoyloxy, preferably acetoxy, or else -O-$CHR^1$-$CHR^2R^3$ (where in this case the compound of the formula III is a symmetrical formaldehyde acetal), in an aprotic solvent such as benzene, toluene, xylene, acetonitrile, dichloromethane or 1,2-dichloroethane or mixtures thereof, under a protective gas atmosphere composed of argon or nitrogen, in the presence of an acid, preferably of a Lewis acid such as aluminum trichloride, aluminum sulfate, boron trifluoride, iron trichloride, gallium trichloride, tin tetrachloride or titanium tetrachloride, or in the presence of iodine or, preferably, trialkylsilyl carboxylates or alkyl-sulfonates, especially trimethylsilyl trifluoromethane-sulfonate, where the amounts of these reagents are 0.01 to 10, preferably 0.3 to 1.3 equivalents, based on the amount of the compound of the formula II employed in each case, at temperatures between −70° C. and +40° C., preferably between −40° C. and +20° C., for 1 to 24 hours, preferably for 2–8 hours. This process provides with good regioselectivity, as a rule>4:1, preferentially the 1H-1 isomer of the particular 1,2,3-triazolo[4,5-d]pyrimidine.

A preferred compound of the formula II is given by $X=-OSi(CH_3)_3$, $Y=CH_3C(O)N(Si(CH_3)_3)-$ and $L_1=-Si(CH_3)_3$. Preferred compounds of the formula III are given by $L_2=-O-CHR^1-CHR^2R^3$, where $R^1$ is isopropoxymethyl or hydrogen, $R^2$ is isopropoxy or hydrogen and $R^3$ is isopropoxymethyl or hydrogen.

The compounds of the formula I according to the invention can have one or more chiral centers in the acyclic side-chain. The compounds are usually in the form of racemates; the pure enantiomers can be prepared or isolated. The invention therefore relates both to the pure enantiomers and to mixtures thereof such as, for example, the relevant racemate.

The present invention furthermore relates to pharmaceuticals with a content of at least one compound according to the invention.

The pharmaceuticals according to the invention can be used enterally (orally), parentsrally (intravenously), rectally or locally (topically). They can be administered in the form of solutions, powders, tablets, capsules (including microcapsules), ointments (creams or gels) or suppositories. Suitable ancillary substances for formulations of these types are the pharmaceutically customary liquid or solid fillers and extenders, solvents, emulsifiers, lubricants, flavorings, colorants and/or buffer substances. The dosage expediently administered is 0.1–10, preferably 0.2–8, mg/kg of body weight. They are expediently administered in dosage units which contain at least the effective daily amount of the compounds according to the invention, for example 30–3, 000, preferably 50–1,000 mg.

The compounds according to the invention can also be administered in combination with other antiviral agents and immunostimulants such as interferons. The tests for antiviral properties and the preparation of the compounds of the formula I according to the invention are described hereinafter:

In vitro tests and results:
HSV-1, HSV-2, HCMV, VZV

The antiviral activity of the test substances on various human pathogenic DNA and RNA viruses was investigated in cell culture test systems. The standard products used are aciclovir (HSV-1, HSV-2) and ganciclovir (CMV, VZV).

The test substances are diluted in ethanol to a final concentration of 1 mg/ml before the test, and Dulbecco's minimal essential medium (MEM) is used for further dilution steps. For the test, serial 3-fold dilutions of the test substances are made up in 96-well microtiter plates. Monkey kidney cells (Veto) in medium199 (5% FCS) or human embryonic diploid pulmonary fibroblast cells MRC-5 (Whittaker) are added in a concentration of $2\times10^4$ cells/well and incubated at 37° C. (5% $CO_2$) for 3 h.

The test mixtures contain the test substance in concentrations from 400 µg/ml to 0.18 µg/ml in MEM supplemented with 4% FCS (HeLa) or 2% FCS (Veto), 100 U/ml penicillin G and 100 µg/ml streptomycin.

The cells are then infected with type 1 herpes simplex virus (corneas), type I herpes simplex virus VR733, type 1 herpes simplex virus VR539 (hominis), type 2 herpes simplex virus VR734 (MS), human cytomegalovirus VR977 or varicella zoster virus VR586 in concentrations at which the cell lawn is completely destroyed within 3 days (CMV: 7 days, VZV: 10 days) (for example HSV-1 corneae: 0.035 PFU/Vero cell, HSV-2: 0.066 PFU/Vero cell).

The cultures are incubated at 37° C. in the presence of 5% $CO_2$. All the investigations are carried out as duplicate determinations; controls are determined only once per plate.

After incubation for 24 h, the cytotoxicity of the test substances is determined by microscopic inspection of the cell cultures. The maximum tolerated dose (MTD) is designated as the highest concentration of product which, under the said test conditions, is insufficient to cause microscopically detectable cell damage.

The untreated infection controls show a complete cytopathogenic effect (CPE) after incubation for a further 48 h (HCMV after 6 days, VZV after 9 days). After microscopic inspection of the cell cultures (HSV, HCMV, VZV), they are then stained (only HSV) with neutral red in accordance with the vital staining method of Finter (1966). The antiviral activity of a test substance is defined as the minimum inhibitory concentration (MIC) which is required to protect 50% of the cells from the cytopathogenic effect of the virus.

The results are compiled in the following table:

TABLE 1

Antiviral activity of exemplary compounds on various herpesviruses in vitro

| Product | MTD (µg/ml) Vero, MRC-5 | MIC (µg/ml) HSV-1 corneae (Vero) | HSV-1 VR733 (Vero) | HSV-1 VR539 (Vero) | HSV-1 labialis (Vero) | HSV-2 VR734 (Vero) | HCMV VR977 (MRC-5) | VZV VR586 (MRC-5) |
|---|---|---|---|---|---|---|---|---|
| Example 9 | ≧333.33 | 1.65 | 1.28 | 4.94 | 1.10 | 2.93 | <0.27 | <0.18 |
| Example 8 | ≧355.56 ≧333.33 | 11.52 | 6.58 | 24.69 | 7.68 | 37.03 | 7.13 | 0.18 |
| Example 10 | ≧311.11 ≧311.11 | 14.81 | 11.52 | 24.69 | 9.88 | 24.69 | <0.30 | <0.18 |
| Ganciclovir | ≧74.07 ≧400.00 | 0.85 | 0.95 | 1.65 | ≦0.18 | 1.93 | 0.06 | 6.13 |
| r Aciclovir | ≧400.00 ≧400.00 ≧400.00 | ≦0.98 | 0.56 | 0.98 | 0.56 | ≦0.40 | 1.16 | 3.01 |

NMRI mice, specific pathogen-free, weighing 15–18 g were infected intraperitoneally with about 50 LD$_{50}$ doses of HSV-1 (frozen material from cell culture). The mice were treated intraperitoneally with the said compounds in the stated doses once 3 hours after the infection and then twice a day (at an interval of 8 hours) for the next 4 days. The control group was treated with physiological saline. The animals were observed for 2 weeks, calculated after the start of the infection. The following table (Table 2) shows the results of this investigation:

TABLE 2

Therapeutic efficacy of the compounds of Examples 9 and 10 in NMRI mice infected intraperitoneally with HSV-1 and treated intraperitoneally or orally

| Compound | Dose μmol/kg | Average survival time (days) | Surviving/ group size | IC$_{50}$* (μmol/ kg) |
|---|---|---|---|---|
| Placebo | 9 × 0 ip | 7.0 ± 1.0 | 0/5 | |
| | 9 × 0 po | 6.8 ± 1.3 | 0/5 | |
| Compound of Example 9 | 9 × 3 ip | 6.3 ± 0.6 | 2/5 | 3.7 |
| | 9 × 10 ip | | 5/5 | |
| | 9 × 30 ip | | 5/5 | |
| | 9 × 3 po | 8.8 ± 1.6 | 0/5 | >30 |
| | 9 × 10 po | 6.2 ± 0.5 | 0/5 | |
| | 9 × 30 po | 8.0 ± 1.7 | 0/5 | |
| Ganciclovir | 9 × 3 ip | 8.0 ± 0 | 3/5 | <3.0 |
| | 9 × 10 ip | | 5/5 | |
| | 9 × 30 ip | | 5/5 | |
| | 9 × 3 po | 11.3 ± 1.5 | 1/5 | 6.8 |
| | 9 × 10 po | 9.5 ± 0.7 | 3/5 | |
| | 9 × 30 po | | 5/5 | |
| Placebo | 9 × 0 ip | 10.4 ± 1.5 | 0/5 | |
| | 9 × 0 po | 8.2 ± 1.1 | 0/5 | |
| Compound of Example 10 | 9 × 9 ip | 11.0 ± 1.4 | 3/5 | <9.0 |
| | 9 × 31 ip | | 5/5 | |
| | 9 × 93 ip | | 5/5 | |
| | 9 × 9 po | 8.8 ± 1.8 | 0/5 | 19.7 |
| | 9 × 31 po | 12.0 | 4/5 | |
| | 9 × 93 po | | 5/5 | |

*from Reed & Muench (1983)

EXAMPLES

1. Compound of the formula I in which X is hydroxyl, Y is acetamido, R$^1$ is isopropoxymethyl, R$^2$ is isopropoxy and R$^3$ is hydrogen:

3.88 g (0.02 mol) of 5-acetamido-7-hydroxy-1H-1,2,3-triazolo[ 4,5-d]pyrimidine (N$^2$-acetyl-8-azaguanine) [prepared by reacting 5-amino-7-hydroxy-1H-1,2,3-triazolo[4, 5-d]-pyrimidine (8-azaguanine) with acetic anhydride and catalytic amounts of N,N-dimethylaminopyridine at the boiling point and subsequent monodeacetylation with saturated aqueous sodium bicarbonate solution, 79.5% of theory, m.p. >280° C., $^1$HNMR (200 MHz, d$_6$-DMSO) δ[ppm]: 16.0 (s, broad, 1H), 12.15 (s, 1H), 11.79 (s, 1H), 2.20 (s, 3H)] are heated to reflux while stirring with 20 ml of dry xylene, 20 ml of hexamethyldisilazane and 0.2 g of ammonium sulfate under an argon atmosphere for 1 h. The solvent and excess hexamethyldisilazane are then removed by distillation in vacuo, and the residue is dissolved in 20 ml of dry 1,2-dichloroethane and added to a solution of 7.3 g (0.02 mol) of formaldehyde bis(1,3-bisisopropoxy-2-propyl) acetal [prepared as described in DE 4020481 A1] in 20 ml of dry 1,2-dichloroethane at −30° C. Then, under an argon atmosphere, 4.7 ml (0.025 mol) of trimethylsilyl trifluoromethanesulfonate are slowly added dropwise to this solution at −30° C. The resulting solution is stirred at −30 to −20° C. for 5 h and subsequently stirred into a cold sodium chloride/saturated sodium bicarbonate solution. The resulting suspension is filtered, the residue is washed with dichloromethane, and the organic phase is separated off. The aqueous phase is extracted several times with dichloromethane; the organic phases are combined, dried over sodium sulfate and concentrated in vacuo. The oily residue is chromatographed (silica gel, mobile phase: ethyl acetate/ n-heptane 2/1) to give as the first fraction 3.18 g (41.6% of theory) of the title compound of Example 1, 5-acetamido-7-hydroxy-1H-1-[(1,3-bisisopropoxy-2-propoxy)methyl]-1,2,3-triazolo [4,5-d]pyrimidine as colorless crystals with melting point 156° C. $^1$H NMR (200 MHz, d$_6$-DMSO) a [ppm]: 12.42 (s, 1H), 11.80 (s, 1H), 6.02 (s, 2H), 4.0–3.85 (m, 1H), 3.5–3.2 (m, 6H), 2.2 (s, 3H), 0.94 (m, 12H). The second fraction obtained is 0.93 g (12.2% of theory) of the isomeric compound 5-acetamido- 7-hydroxy-3H-3-[(1,3-bisisopropoxy-2-propoxy)methyl]- 1,2,3-triazolo[4,5-d]pyrimidine as colorless crystals with melting point 95° C and the $^1$H NMR spectrum (200 MHz, d$_6$-DMSO)δ[ppm]: 12.21 (s, broad, 1H), 12.05 (s, broad, 1H), 5.85 (s, 2H), 3.9–3.79 (m, 1H), 3.5–3.2 (m, 6H), 2.12 (s, 3H), 0.95 (m, 12H).

2. Compound of the formula I in which X is hydroxyl, Y is amino, R$^1$ is isopropoxymethyl, R$^2$ is isopropoxy and R$^3$ is hydrogen:

0.5 g (1.3 retool) of the compound of Example 1 is heated under reflux with 10 ml of methanol and 10 ml of a 40% strength aqueous methylamine solution for 2 h; the clear solution is concentrated to about ⅓ of its volume in vacuo and acidified with 2 N acetic acid. The resulting suspension is cooled and filtered, and the filtrate is washed twice with cold water and subsequently once each with isopropyl ether and diethyl ether and subsequently dried. 0.43 g (97.3% of theory) of 5-amino-7-hydroxy- 1H-1-[(1,3-hisisopropoxy)-2-propoxy)methyl]-1,2,3-triazolo[ 4,5-d]pyrimidine is obtained as colorless crystals with melting point 227° C. (decomposition). $^1$H NMR (200 MHz, d$_6$-DMSO) δ[ppm]: 11.25 (s, 1H), 6.45 (s, 2H), 5.91 (s, 2H), 3.95–3.83 (m, 1H), 3.5–3.18 (m, 6H), 0.95 (m, 12H).

3. Compound of the formula I in which X is hydroxyl, Y is acetamido, R$^1$ is hydroxymethyl, R$^2$ is hydroxyl and R$^3$ is hydrogen:

1.53 g (4 mmol) of the compound of Example 1 are dissolved in 25 ml of dry dichloromethane (argon atmosphere). To this solution are slowly added dropwise, while stirring at −60° C., 20 ml (20 mmol) of a 1 molar solution of boron trichloride in dichloromethane. The resulting solution is stirred at −40 to −30° C. for 5 h; then, at −60° C., a mixture of 20 ml of methanol and 20 ml of dichloromethane is slowly added dropwise before about 8 ml of triethylamine are added. The solution is stirred at room temperature for 1 h and then evaporated to dryness in vacuo, the residue is dissolved in a little water, an excess of sodium carbonate is added, and the mixture is again completely evaporated in vacuo. The residue is suspended in a little warm methanol, filtered off with suction and washed with methanol. The filtrate is completely evaporated and chromatographed (silica gel; mobile phase: dichloromethane/methanol 5/1). The chromatography provides 0.3 g (25.2% of theory) of 5-acetamido-7-hydroxy-1H-1-[(1,3-dihydroxy-2-propoxy)methyl] -1,2,3-triazolo[4,5-d]pyrimidine as colorless crystals with melting point 176° C. $^1$H NMR (200 MHz, d$_6$-DMSO) δ[ppm]: 12.42 (s, 1H), 11.80 (s, 1H), 6.05 ( s, 2H), 4.55 ( t, 2H), 3.73 (m, 1H), 3.48–3.15 (m, 4H), 2.2 (s, 3H).

4. Compound of the formula I in which X is hydroxyl, Y is amino, R$^1$ is hydroxymethyl, R$^2$ is hydroxyl and R$^3$ is hydrogen:

0.25 g (0.84 mmol) of the compound of Example 3 is heated to reflux in 10 ml of 40% strength aqueous methylamine solution for 2 h and then completely evaporated in vacuo. The residue is dissolved in a little warmwater, neutralized with 2 N acetic acid and completely evaporated in vacuo. The residue is suspended in cold ethanol, filtered off with suction and washed with ethanol and diethyl ether. Crystallization from water results in 0.2 g (93% of theory) of 5-amino-7-hydroxy-1H-1-[(1,3-dihydroxy 2-propoxy)methyl]-1,2,3-triazolo[4,5-d]pyrimidine as colorless crystals with melting point >290° C. $^1$H NMR (200 MHz, d$_6$-DMSO) δ[ppm]: 11.25 (s, 1H), 6.50 (s, 2H), 5.95 (s, 2H), 4.55 (t, 2H), 3.70 (m, 1H), 3.45–3.10 (m, 4H).

5. Compound of the formula I in which X is mercapto, Y is acetamido, $R^1$ is isopropoxymethyl, $R^2$ is isopropoxy and $R^3$ is hydrogen:

5.73 g (15 retool) of the compound of Example 1 in 225 ml of dry toluene are stirred with 6.7 g (16.5 mmol) of 2,4-bis(4-methoxyphenyl)-1,3-dithia-2,4-diphosphetan 2,4-disulfide at 85° C. under an argon atmosphere for 3 h. The reaction mixture is subsequently concentrated in vacuo and chromatographed ( silica gel; mobile phase: ethyl acetate/ n-heptane ⅔). 2.7 g (45% of theory) of 5-acetamido-7-mercapto-1H-1-[(1,3-bisisopropoxy-2-propoxy) methyl] -1,2,3 -triazolo [4,5-d]pyrimidine are obtained as yellow crystals with melting point 91° C. $^1$H NMR (200 MHz, d$_6$-DMSO) δ[ppm]: 13.79 (s, 1H), 12.05 (s, 1H), 6.35 (s, 2H), 4.05–3.92 (m, 1H), 3.5–3.24 (m, 6H), 2.24 (s, 3H), 0.94 (m, 12H).

6. Compound of the formula I in which X is hydrogen, Y is acetamido, $R^1$ is isopropoxymethyl, $R^2$ is isopropoxy and $R^3$ is hydrogen:

0.6 g (1.5 retool) of the compound of Example 5 is dissolved in 60 ml of absolute ethanol, about 3 g of Raney nickel (washed with ethanol) are added, then the mixture is heated to reflux for 3 h and, while still hot, filtered to remove Raney nickel and concentrated in vacuo. Chromatography on silica gel with ethyl acetate/n-heptane ⅔ results in 0.25 g (45.5% of theory) of 5-acetamido-1H-1-[(1,3-bisisopropoxy-2-propoxy)methyl]- 1,2,3-triazolo[4,5-d]pyrimidine as colorless crystals with melting point 104° C. $^1$H NMR (200 MHz, d$_6$-DMSO) δ[ppm]: 10.88 (s, 1H), 9.55 (s, 1H), 6.25 (s, 2H), 3.82–3.72 (m, 1H), 3.45–3.10 (m, 6H), 2.22 (s, 3H), 0.88 (s, 12H) .

7. Compound of the formula I in which X is hydrogen, Y is amino, $R^1$ is isopropoxymethyl, $R^2$ is isopropoxy and $R^3$ is hydrogen:

0.5 g (1.37 mmol) of the compound of Example 6 is treated with 40% strength aqueous methylamine solution as in Example 2 and provides, after purification by chromatography (silica gel; mobile phase: ethyl acetate/methanol 9/1), 0.40 g (90.1% of theory) of 5-amino-1H-1-[(1,3-bisisopropoxy- 2-propoxy)methyl]-1,2,3-triazolo[4,5 -d]pyrimidine as colorless crystals with melting point 87° C. $^1$H NMR (270 MHz, d$_6$-DMSO) δ[ppm]: 9.18 (s, 1H) , 6.92 (s, 2H), 6.10 (s, 2H), 3.77–3.67 (m, 1H), 3.47–3.25 (m, 6H), 0.92 (d, 12H).

8. Compound of the formula I in which X is hydrogen, Y is acetamido, $R^1$ is hydroxymethyl, $R^2$ is hydroxyl and $R^3$ is hydrogen:

1.15 g (3.14 mmol) of the compound of Example 6 are dissolved in 20 ml of dry dichloromethane (argon atmosphere). To this solution are slowly added dropwise, at –60° C. while stirring, 12.56 ml (12.56 mmol) of a 1 molar solution of boron trichloride in dichloromethane. The resulting solution is stirred at –40 to –30° C. for 5 h; then, at –60° C., a mixture of 12.5 ml of methanol and 12.5 ml of dichloromethane is slowly added dropwise before about 5 ml of triethylmine are added. The solution is stirred at room temperature for 1 h and then evaporated to dryness in vacuo. The residue is purified by chromatography (silica gels mobile phase: ethyl acetate/isopropanol/water 4/3/0.3). The chromatography provides 0.55 g (62.1% of theory) of 5-acetamido- 1H-1-[(1,3-dihydroxy-2-propoxy)methyl]-1,2,3-triazolo[ 4,5-d]pyrimidine as colorless crystals with melting point 167–168° C. $^1$H NMR (200 MHz, d$_6$-DMSO) δ[ppm]: 10.9 (s, 1H), 9.58 (s, 1H), 6.27 (s, 2H), 4.63 (t, 2H), 3.65–3.5 (m, 1H), 3.5–3.18 (m, 4H), 2.23 (s, 3H).

9. Compound of the formula I in which X is hydrogen, Y is amino, $R^1$ is hydroxymethyl, $R^2$ is hydroxyl and $R^3$ is hydrogen:

0.5 g (1.78 mmol) of the compound of Example 8 is dissolved in a mixture of 10 ml of methanol and 10 ml of 40% strength aqueous methylamine solution while stirring and heated to reflux for 2 h. The resulting solution is diluted with a little aqueous methanol, boiled with active carbon and filtered, and the residue is washed twice with ethanol. The combined filtrates are concentrated, the residue is stirred with cold ethanol, and the resulting suspension is filtered and washed with a little ethanol and diethyl ether. The residue is recrystallized from ethanol and provides 0.35 g (81.9% of theory) of 5-amino-1H-1-[(1,3-dihydroxy-2-propoxy)methyl]-1,2,3-triazolo[ 4,5-d]pyrimidine as colorless crystals with melting point 161° C. $^1$H NMR (200 MHz, d$_6$-DMSO) δ[ppm]: 9.19 (s, 1H), 6.91 (s, 2H), 6.13 (s, 2H), 4.61 (t, 2H), 3.60–3.23 (m, 5H).

10. Compound of the formula I in which X is hydrogen, Y is amino, $R^1$ is acetoxymethyl, $R^2$ is acetoxy and $R^3$ is hydrogen:

0.24 g (1 mmol) of the compound of Example 9 is suspended in 10 ml of anhydrous acetonitrile and, while stirring, 40 mg of 4-dimethylaminopyridine and 0.6 g (2.9 mmol) of dicyclohexylcarbodiimide and 0.17 ml (0,175 g, 2.9 mmol) of glacial acetic acid are added. The mixture is stirred at room temperature for 2 h and then 23.5 ml of isopropanol and 23.5 ml of water are added and the mixture is stirred for a further 15 min. The precipitate (dicyclohexylurea) is filtered off, the residue is washed with tetrahydrofuran, and the clear filtrate is completely evaporated. The crystalline residue is chromatographed on silica gel with a mixture of 20 parts of ethyl acetate and 1 part of methanol. This results—after crystallization from isopropanol—in 0.29 g (89.5% of theory) of 5-amino-1H-1-[(1,3-diacetoxy-2-propoxy)methyl]-1,2,3-triazolo [4,5-d]pyrimidine as colorless crystals with melting point 143–144° C. $^1$H NMR (200 MHz, d$_6$-DMSO) δ[ppm]: 9.2 (s, 1H), 6.97 (s, 2H), 6.12 (s, 2H), 4.15–3.95 (m, 5H), 1.79 (s, 3H) .

11. Compound of the formula I in which X is hydroxyl, Y is acetamido, $R^1$ is hydrogen, $R^2$ is isopropoxy and $R^3$ is hydrogen:

0.5 g of ammonium sulfate is added to 9.7 g (0.05 mol) of 5-acetamido-7-hydroxy-1H-1,2,3-triazolo[4,5-d]pyrimidine in a mixture of 50 ml of dry xylene and 50 ml of hexamethyldisilazane, and the mixture is boiled under reflux under an argon atmosphere for 1.5 h. The resulting solution is completely evaporated with exclusion of moisture and dissolved in 50 ml of dry 1,2-dichloroethane. To this solution is added a solution of 11 g (0.05 mol) of formaldehyde bis(isopropoxyethyl)acetal in 50 ml of dry 1,2-dichloroethane, and the mixture is cooled to –30° C. and, while stirring, a solution of 12 ml (0.065 mol) of trimethylsilyl trifluoromethanesulfonate is slowly added. The reaction mixture is stirred at –30° C. for 5 h and then poured into a saturated aqueous sodium bicarbonate solution and neutralized with acetic acid. The resulting suspension is filtered then the residue is washed with dichloromethane; the organic phase is then separated off, dried over sodium sulfate and completely evaporated, and the crystalline residue which is composed of an N1/N3 isomer mixture is purified by crystallization from ethanol. 5.7 g (36.8% of theory) of 5-acetamido 7-hydroxy-1H-1-[(2-isopropoxyethoxy)methyl]-1,2,3-triazolo[ 4,5-d]pyrimidine are obtained as colorless crystals with melting point 190–191° C., $^1$H NMR (200 MHz, $d_6$-DMSO) δ[ppm]: 12.42 (s, 1H), 11.80 (s, 1H), 6.0 (s, 2H), 3.70–3.64 (m, 2H), 3.53–3.40 (m, 3H), 2.2 (s, 3H), 1.0 (d, 6H), in addition to 2.25 g (14.5% of theory) of 5-acetamido-7-hydroxy-3H-3-[(2-isopropoxyethoxy)methyl]-1,2,3-triazolo[4,5-d]pyrimidine as colorless crystals with melting point 165–166° C.; $^1$H NMR (270 MHz, $d_6$-DMSO) δ[ppm]: 12.15 (s, broad, 2H), 5.8 (s, 2H), 3.7–3.64 (m, 2H), 3.56–3.42 (m, 3H), 2.22 (s, 3H), 1.02 (d, 6H).

12. Compound of the formula I in which X is mercapto, Y is acetamido, $R^1$ is hydrogen, $R^2$ is isopropoxy and $R^3$ is hydrogen:

0.93 g (0.003 mol) of the compound of Example 11 in 45 ml of dry toluene is stirred with 1.34 g (0.0033 mol) of 2,4 - bis ( 4 -methoxyphenyl)-1,3-dithia-2,4-diphosphetane 2,4-disulfide at 85° C. under an argon atmosphere for 3 h. The reaction mixture is subsequently concentrated in vacuo and chromatographed ( silica gel; mobile phase: ethyl acetate/ n-heptane 2/1). 0.35 g (35.8% of theory) of 5-acetamido-7-mercapto-1H-1-[(2 -isopropoxyethoxy)methyl]- 1,2,3 - triazolo [4,5 -d] pyrimidine is obtained as pale yellow crystals with melting point 154–156° C; $^1$H NMR (200 MHz, $d_6$-DMSO) δ[ppm]: 13.8 (s, lB), 12.05 (s, 1H), 6.31 (s, 2H), 3.74–3.68 (m, 2H), 3.57–3.40 (m, 3H), 2.22 (s, 3H), 1.0 (d, 6H). Isolated as byproduct is 0.12 g (11.7% of theory) of 5-thioacetamido-7-mercapto-1H- 1-[(2-isopropoxyethoxy)methyl]-1,2,3-triazolo [4,5 -d] pyrimidine (compound of the formula I, in which X is mercapto, Y is thioacetamido, $R^1$ is hydrogen, $R^2$ is isopropoxy and $R^3$ is hydrogen) as yellow crystals with melting point 173° C. $^1$H NMR (200 MHz, $d_6$-DMSO) δ[ppm]: 15.22 (s, broad, 1H), 13.10 (s, broad, 1H), 6.35 (s, 2H), 3.78–3.68 (m, 2H), 3.57–3.40 (m, 3H), 2.76 (s, 3H), 1.01 (d, 6H).

13. Compound of the formula I in which X is hydrogen, Y is amino, $R^1$ is hydrogen, $R^2$ is isopropoxy and $R^3$ is hydrogen:

1.25 g (0.0038 mol) of the compound of Example 12 are dissolved in 18.5 ml of n-propanol, 15 g of Raney nickel are added, and the mixture is boiled under reflux with stirring for 3 h. The reaction mixture is then filtered hot, the residue is washed with n-propanol, and the filtrate is concentrated. The residue is purified by chromatography (silica gel; mobile phase: ethyl acetate/ethanol 20/0.5). 0.6 g (62.6% of theory) of 5-amino-lH-1-[(2 -isopropoxyethoxy)methyl]-1, 2,3-triazolo-[ 4,5-d]pyrimidine is obtained as colorless crystals with melting point 121–122° C.; $^1$H NMR (200 MHz, $d_6$-DMSO) δ[ppm]. 9.21 (s, 1H), 6.95 (s, 2H), 6.05 (s, 2H), 3.64–3.55 (m, 2H), 3.51–3.36 (m, 3H), 0.98 (d, 6H).

14. Compound of the formula I in which X is hydrogen, Y is amino, $R^1$ is hydrogen, $R^2$ is hydroxyl and $R^3$ is hydrogen:

0.252 g (0.001 mol) of the compound of Example 13 is dissolved in 20 ml of dry dichloromethane and, while stirring under an argon atmosphere at −60° C., 3 ml of a 1 molar solution of boron trichloride in dichloromethane are added, and the mixture is stirred at −60° C. for 5 h and at −50° C. to −40° C. for 1 h. Then, at −60° C, 3 ml of methanol dissolved in 3 ml of dichloromethane, and 1.6 ml of triethylamine, are added, the mixture is allowed to warm to room temperature and stirred at this temperature for a further half h, and the resulting mixture is concentrated in vacuo. The residue is dissolved in a little water, 0.8 g of sodium carbonate (dissolved in the necessary amount of water) is added, and the mixture is heated to 50° C. and completely evaporated in vacuo. The residue obtained in this way is dissolved in hot methanol, filtered, washed with methanol, concentrated and purified by chromatography (silica gel; mobile phase: ethyl acetate/methanol 9/1). 0.16 g (76.2% of theory) of 5-amino-1H-1-[(2-hydroxyethoxy)methyl]-1,2,3-triazolo-[ 4,5-d]pyrimidine is obtained as colorless crystals with melting point 168° C.; $^1$H NMR (200 MHz, $d_6$-DMSO) δ[ppm]: 9.22 (s, 1H), 6.97 (s, 2H), 6.05 (s, 2H), 4.66 (t, 1H), 3.48 (m, 4H) .

15. Compound of the formula I in which X is hydrogen, Y is amino, $R^1$ is hydrogen, $R^2$ is acetoxy and $R^3$ is hydrogen:

0.21 g (0.001 mol) of the compound of Example 14 is suspended with stirring in 10 ml of dry acetonitrile with the addition of 20 mg of 4-dimethylaminopyridine, 0.3 g (0.00145 mol) of N,N'-dicyclohexylcarbodiimide and 0.09 ml (0.00145 mol) of acetic acid and stirred at room temperature for 12 h. Then 23.5 ml of water and 23.5 ml of isopropanol are added to the reaction mixture, which is then stirred for 15 min and filtered, the residue is washed with tetrahydrofuran, and the filtrate is concentrated in vacuo. The residue is chromatographed (silica gel; mobile phase: methyl tert.butyl ether/ethanol 20/1) to obtain 0.2 g (79.4% of theory) of 5-amino-1H-1-[(2-acetoxyethoxy)methyl-1,2, 3-triazolo-[ 4,5-d]pyrimidine as colorless crystals with melting point 138° C.; $^1$H NMR (200 MHz, $d_6$-DMSO) δ[ppm]: 9.23 (s, 1H), 6.98 (s, 2H), 6.08 (s, 2H), 4.08 (m, 2H), 3.70 (m, 2H) 1.90 (s, 3H).

We claim:

1. A compound of the formula I

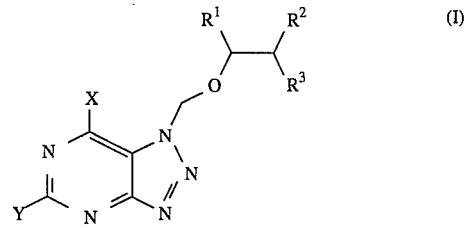

and its tautomeric forms, in which

X is hydrogen, halogen, hydroxyl, $C_1$-$C_6$-alkoxy, benzyloxy, phenoxy, mercapto, $C_1$-$C_6$-alkylthio, benzylthio, phenylthio or amino, Y is amino, $C_1$-$C_8$-acylamino, $C_1$-$C_8$-thioacylamino, $C_2$-$C_{16}$-diacylamino, $C_2$-$C_{16}$-di(thioacyl)amino, ($C_1$-$C_4$-alkyl)$_2$-N-CH=N- or N-($C_1$-$C_4$-alkyl)pyrrolidinylidene-N-, $R^1$ is hydrogen, $C_1$-$C_6$-alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_6$-acyloxy, $C_1$-$C_8$-acylamino or $C_1$-$C_8$-acylthio group or by a radical $R^4$ where $R^4$ is -P(O)(OR$^5$)(OR$^6$) or -O-CH$_2$-P(O)(OR$^5$)(OR$^6$) in which $R^5$ and $R^6$ are, independently of one another, hydrogen or a $C_1$-$C_6$-alkyl radical or ammonium or triethylammonium or an alkali metal ion, $R^2$ is hydrogen, $C_1$-$C_6$-alkyl, hydroxyl, amino, mercapto, halogen, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino, $C_1$-$C_8$-acylthio or -O-$CH_2$-P(O) ($OR^5$) ($OR^6$) where the radicals $R^5$ and $R^6$ are as defined above, and $R^3$ is hydrogen, $C_1$-$C_6$0alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P(O) ($OR^5$)($OR^6$) or -O-$CH_2$-P(O) ($OR^5$)($OR^6$) in which $R^5$ and $R^6$ are, independently of one another, hydrogen or a $C_1$-$C_6$-alkyl radical or ammonium, triethylammonium or an alkali metal ion, and its physiologicallytolerated salts and evident chemical equivalents with the proviso that X is not hydroxyl when $R^1$ and $R^3$ are hydrogen and $R^2$ is benzoyloxy.

2. A compound of the formula I as claimed in claim 1, in which

X is hydrogen, hydroxyl, $C_1$-$C_6$-alkoxy, benzyloxy, mercapto or amino,

Y is amino, $C_1$-$C_3$-acylamino, $C_1$-$C_3$-thioacylamino, $C_2$-$C_6$-diacylamino, $C_2$-$C_6$-di(thioacayl)amino, $(CH_3)_2$-N-CH=N- or N-$(CH_3)$-pyrrolidinylidene-N-, $R^1$ is hydrogen, $C_1$-$C_3$-alkyl optionally substituted by a hydroxyl, $C_1$-$C_6$-alkoxy or $C_1$-$C_8$-acyloxy group or by a radical $R^4$ where $R^4$ is -P(O) ($OR^5$) ($OR^6$) are, independently of one another, hydrogen or a $C_1$-$C_6$-alkyl radical or ammonium or triethylammonium or an alkali metal ion, $R^2$ is hydrogen, hydroxyl, $C_1$-$C_6$-alkoxy or $C_1$-$C_8$-acyloxy or -O-$CH_2$-P(O) ($OR^5$) ($OR^6$) where the radicals $R^5$ and $R^6$ are as defined above, and $R^3$ is hydrogen or $C_1$-$C_4$-alkyl optionally substituted by a hydroxyl, $C_1$-$C_6$-alkoxy or $C_1$-$C_8$-acyloxy group or by a radical $R^4$ where $R^4$ is -P(O)($OR^5$) ($OR^6$) or -O-$CH_2$-P (O) ($OR^5$) ($OR^6$) in which $R^5$ and $R^6$ are, independently of one another, hydrogen or a $C_1$-$C_6$-alkyl radical or ammonium, triethylammonium or an alkali metal ion.

3. A compound of the formula I as claimed in claim 1, in which

X is hydrogen, hydroxyl, SH or amino,

Y is amino or $C_1$-$C_3$-acylamino, $R^1$ is $C_1$-$C_3$-alkyl optionally substituted by a hydroxyl, $C_1$-$C_3$-alkoxy or $C_1$-$C_3$-acyloxy group, $R^2$ is hydroxyl, $C_1$-$C_3$-alkoxy or $C_1$-$C_3$-acyloxy, and $R^3$ is hydrogen.

4. A method for the treatment of viral diseases which comprises administering an amount effective for such treatment of a compound of the formula I

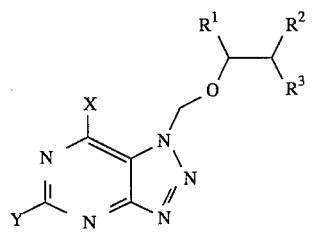

(I)

or a tautomeric form thereof, in which

X is hydrogen, halogen, hydroxyl, $C_1$-$C_6$-alkoxy, benzyloxy, phenoxy, mercapto, $C_1$-$C_6$-alkylthio, benzylthio, phenylthio or amino, Y is amino, $C_1$-$C_8$-acylamino, $C_1$-$C_8$-thioacylamino, $C_2$-$C_{16}$-diacylamino, $C_2$-$C_{16}$-di(thioacyl)amino, ($C_1$-$C_4$-alkyl)$_2$-N-CH=N- or N-($C_1$-$C_4$-alkyl)pyrrolidinylidene-N-, $R^1$ is hydrogen, $C_1$-$C_6$-alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P(O)($OR^5$)($OR^6$) or -O-$CH_2$-P(O)($OR^5$)($OR^6$) in which $R^5$ and $R^6$ are, independently of one another, hydrogen or a $C_1$-$C_6$-alkyl radical or ammonium or triethylammonium or an alkali metal ion, $R^2$ is hydrogen, $C_1$-$C_6$-alkyl, hydroxyl, amino, mercapto, halogen, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino, $C_1$-$C_8$-acylthio or -O-$CH_2$-P(O)($OR^5$)($OR^6$) where the radicals $R^5$ and $R^6$ are as defined above, and $R^3$ is hydrogen, $C_1$-$C_6$-alkyl optionally substituted by halogen or by a hydroxyl, amino, mercapto, $C_1$-$C_6$-alkoxy, $C_1$-$C_6$-alkylthio, $C_1$-$C_6$-alkylamino, benzyloxy, benzylthio, benzylamino, phenoxy, phenylthio, $C_1$-$C_8$-acyloxy, $C_1$-$C_8$-acylamino or $C_1$-$C_8$-acylthio group or by a radical $R^4$ where $R^4$ is -P(O)($OR^5$)($OR^6$) or -O-$CH_2$-P(O)($OR^5$)($OR^6$) in which $R^5$ and $R^6$ are, independently of one another, hydrogen or a $C_1$-$C_6$-alkyl radical or ammonium, triethylammonium or an alkali metal ion, or a physiologically tolerated salt or evident chemical equivalent thereof.

5. A pharmaceutical composition comprising a pharmaceutically effective content of at least one compound of the formula I as claimed in claim 1 together with a pharmaceutically acceptable excipient.

6. A method for the production of a pharmaceutical composition for the treatment of viral diseases which comprises incorporating in said pharmaceutical composition an amount effective for such treatment of a compound of the formula I as claimed in claim 1.

7. A method for the treatment of viral diseases which comprises administering an amount effective for such treatment of a compound of the formula I as claimed in claim 1.

8. A method for the treatment of viral diseases which comprises administering in need of such treatment a pharmaceutical composition as claimed in claim 5.

\* \* \* \* \*

UNITED STATES PATENT AND TRADEMARK OFFICE
CERTIFICATE OF CORRECTION

PATENT NO. : 5,457,091

DATED : October 10, 1995

INVENTOR(S) : Gerhard JAEHNE et al.

It is certified that error appears in the above-indentified patent and that said Letters Patent is hereby corrected as shown below:

Claim 1, col. 12, line 60, "$C_1-C_6-$" should read --$C_1-C_8-$ --;

col. 13, line 6, "$C_1-C_6 0alkyl$" should read --$C_1-C_6-alkyl$--.

Claim 2, col. 13, line 29, after "$(OR^6)$", insert --or $-O-CH_2-P(O)(OR^5)(OR^6)$ in which $R^5$ and $R^6$--;

line 33, "alkoxyor" should read --alkoxy or--.

Claim 8, col. 14, line 61, delete "in need of such treatment--.

Signed and Sealed this

Twenty-first Day of April, 1998

Attest:

BRUCE LEHMAN

*Attesting Officer*     *Commissioner of Patents and Trademarks*